United States Patent [19]

Howell et al.

[11] 3,951,167
[45] Apr. 20, 1976

[54] FLUID HANDLING ASSEMBLY

[75] Inventors: Gary W. Howell, Elkton, Md.;
Danahey Ryan, Newark, Del.

[73] Assignee: E. I. Du Pont de Nemours and Company, Wilmington, Del.

[22] Filed: Dec. 5, 1974

[21] Appl. No.: 530,034

[52] U.S. Cl............................... 137/608; 137/604; 251/331
[51] Int. Cl.²........................................ F16K 11/10
[58] Field of Search ............ 137/604, 608; 251/331

[56] References Cited
UNITED STATES PATENTS

| | | | |
|---|---|---|---|
| 2,139,919 | 12/1938 | Watkins | 137/604 |
| 3,477,693 | 11/1969 | Bezanis | 251/331 |
| 3,575,348 | 4/1971 | MacKay | 137/604 |
| 3,601,318 | 8/1971 | Gearing et al. | 137/604 |

FOREIGN PATENTS OR APPLICATIONS

| | | | |
|---|---|---|---|
| 897,418 | 5/1962 | United Kingdom | 137/604 |
| 910,188 | 11/1962 | United Kingdom | 137/604 |

Primary Examiner—William R. Cline
Assistant Examiner—H. Jay Spiegel

[57] ABSTRACT

Disclosed herein is a fluid handling assembly comprising a multi-valve assembly, a probe connected to a first valve structure in said multi-valve assembly, a plurality of secondary fluid sources connected to secondary valve in said multi-valve assembly and a pump connected to said multi-valve assembly. Each of the valves in the multi-valve assembly comprise valve seats, flexible diaphragms coacting with the valve seat to form leak-tight chambers containing orifices connecting the various channels in the valves, and a means to move the diaphragm to close off the connection between the orifices and thereby shut the valve.

11 Claims, 5 Drawing Figures

FLUID HANDLING ASSEMBLY

BACKGROUND OF THE INVENTION

1. Field of the Invention:

This invention relates to a fluid handling and sampling assembly. More particularly, this invention relates to a multi-valve assembly for use in an analytical instrument.

2. Description of the Prior Art:

The heart of many analytical systems, particularly chemical analyzers which have become so popular in the last few years, is the fluid handling assembly. This assembly is designed to inject precise amounts of sample fluid along with precise amounts of various buffers or diluent into the compartments where the reaction takes place. Of prime concern in such assemblies is the precision with which small amounts of fluid can be handled. The key to their precision lies partially in the pump assembly and partially in the valve assembly.

The valve assemblies used in the original versions of such analytical devices were often complicated, expensive devices which required considerable maintenance and repair. As the precision of such devices increased, more emphasis has been placed on the ability to design reliable, care-free systems which are both inexpensive and easy to maintain.

One representative fluid handling assembly is described in U.S. Pat. No. 3,612,360 which discloses a piston pump in conjunction with a plurality of separate pistontype valves. While such a system performs quite adequately, each valve consists of a large number of parts which must be precision-milled from a suitable material such as stainless steel. Such a system is extremely expensive, and its maintenance and repair requires a considerable amount of time and effort.

The present invention relates to a fluid handling assembly of a simple design; one that is precise, simple to construct and easy to maintain.

SUMMARY OF THE INVENTION

The fluid handling assembly comprises:
a. a housing;
b. a primary channel in the housing, a first end of which terminates at a pump orifice on the surface of the housing;
c. an output channel in the housing, a first end of which terminates at an intake/output orifice on the surface of the housing;
d. a first valve structure comprising;
  i. a first valve seat disposed in the housing and containing first and second closely spaced orifices, one orifice being connected to the second end of the primary channel and the other orifice being connected to the second end of the output channel;
  ii. first chamber forming means coacting with the first valve seat to form a leak-tight first chamber connecting the first and second orifices of the first valve seat;
  iii. first closure means movably mounted in the first chamber and having a resilient surface to mate with the first valve seat; and
  iv. first means to move the resilient surface of the first closure means into contact with the first valve seat to close off the connection between the first and second orifices of the first valve seat; and
e. at least one secondary valve structure comprising
  i. a secondary valve seat disposed in the housing and containing two closely spaced orifices;
  ii. a secondary channel connecting one orifice of the secondary valve seat to the primary channel;
  iii. an input channel connecting the other orifice of the secondary valve seat to an input orifice located on the surface of the housing;
  iv. secondary chamber forming means coacting with the secondary valve seat to form a leak-tight secondary chamber connecting the orifices of the second valve seat;
  v. secondary closure means movably mounted in the secondary chamber and having a resilient surface to mate with the secondary valve seat; and
  vi. secondary means to move the resilient surface of the secondary closure means into contact with the secondary valve seat to close off the connection between the orifices of the secondary valve seat.

In a preferred embodiment, the chamber forming means comprise flexible diaphragms connected at their periphery to the housing and coacting with the valve seats to form the leak-tight chambers. In a still more preferred embodiment, the valve seats are located in blind recesses within the housing, the means to move are solenoids which threadedly engage the housing, and each secondary channel is disposed directly opposite another secondary channel.

In a still more preferred embodiment, the first valve structure of the multi-valve assembly contains a third orifice in its valve seat which is located within the periphery of the first diaphragm but spaced relatively distant from the first and second orifices. The valve assembly further comprises a delimiting means which coacts with the first diaphragm to press the peripheral portion of the diaphragm into contact with the valve seat and limit the extent of the first chamber so that it connects only the first and second orifices. The delimiting means is, however, resiliently mounted so that it will retract under sufficient pressure and expand the first chamber to include the third orifice.

This multi-valve assembly is used in a fluid handling assembly which further comprises a probe connected to the intake/output orifice of the valve assembly through a flexible tube, and a plurality of secondary fluid sources connected to the input orifices of the valve assembly through suitable tubes. A pump is disposed adjacent and connected to the pump orifice. Finally, the first means to move is normally positioned so that the first valve structure is in a normally-open mode, and the second means to move is normally positioned so that the secondary valve structure is in a normally-closed mode. In this embodiment, there is a normally-open path between the pump and the probe, and the secondary channels leading from the multi-valve assembly to the sources of secondary fluid are normallyclosed.

BRIEF DESCRIPTION OF THE DRAWINGS

The operation and advantages of the present invention can best be described by reference to the following figures in which.

DISCUSSION OF THE DRAWINGS

Figure 1:
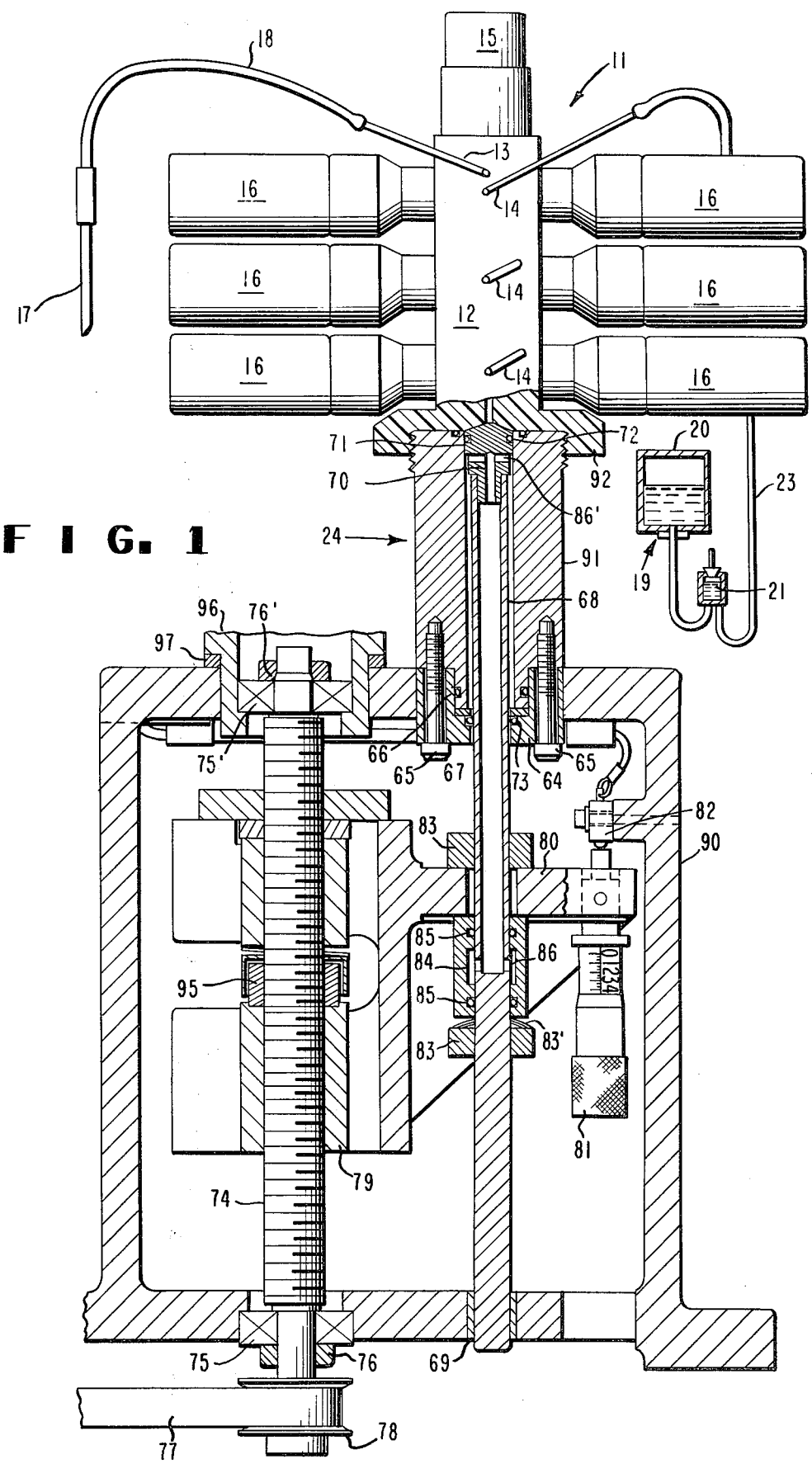
FIG. 1 is a side view of one embodiment of the fluid handling assembly of the present invention showing one embodiment of the pump in cross-section.
Figure 2:
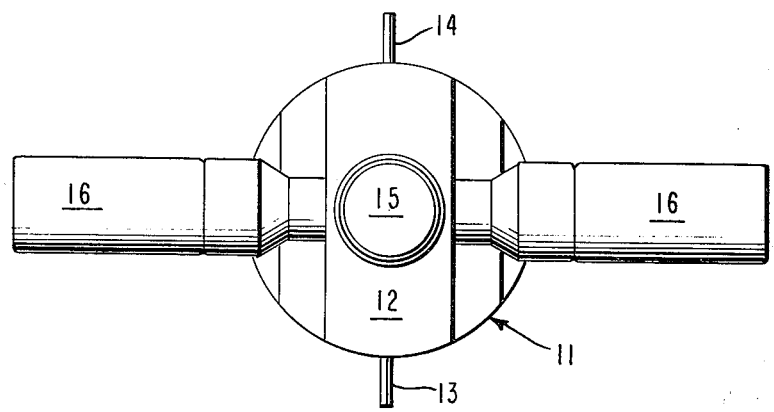
FIG. 2 is a full top view of the multi-valve assembly shown in FIG. 1.

Referring to FIGS. 1 and 2, the fluid handling assembly comprises a multi-valve assembly 11 generally including a housing 12, a first valve structure indicated generally by 15 and a plurality of secondary valve structures indicated generally by 16. A movable probe 17 is connected to output channel 27 through flexible tube 18 and intake/output tube 13. A source of secondary fluid indicated generally by 19 is also included. This source includes a container 20 for secondary liquid, connected to intake tubes 14 through a debubbler 21 and connecting lines 22 and 23. Also connected to the housing of the multivalve assembly is a pump indicated generally by 24.

Figure 3:
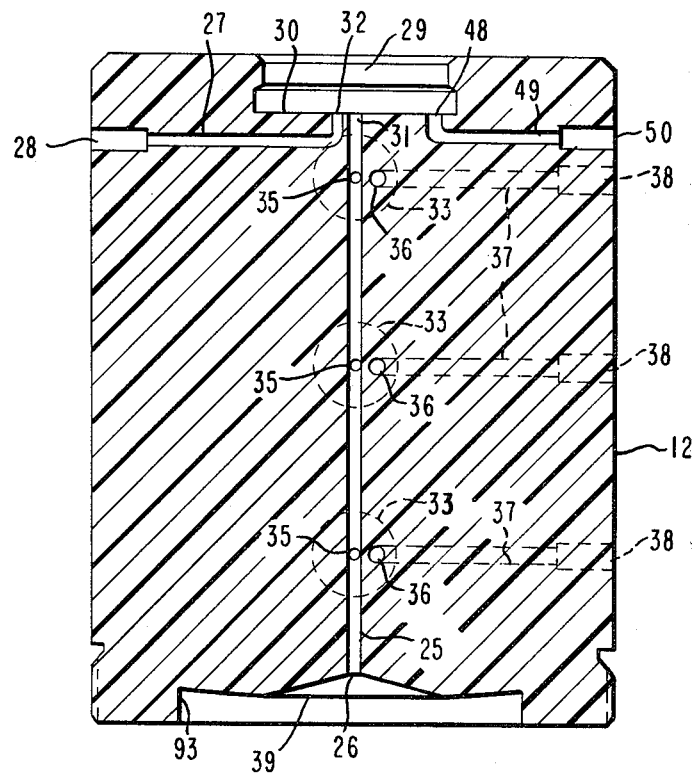
FIG. 3 is a cross-sectional side view of the housing used in the multi-valve assembly shown in FIGS. 1 and 2.
Figure 4:
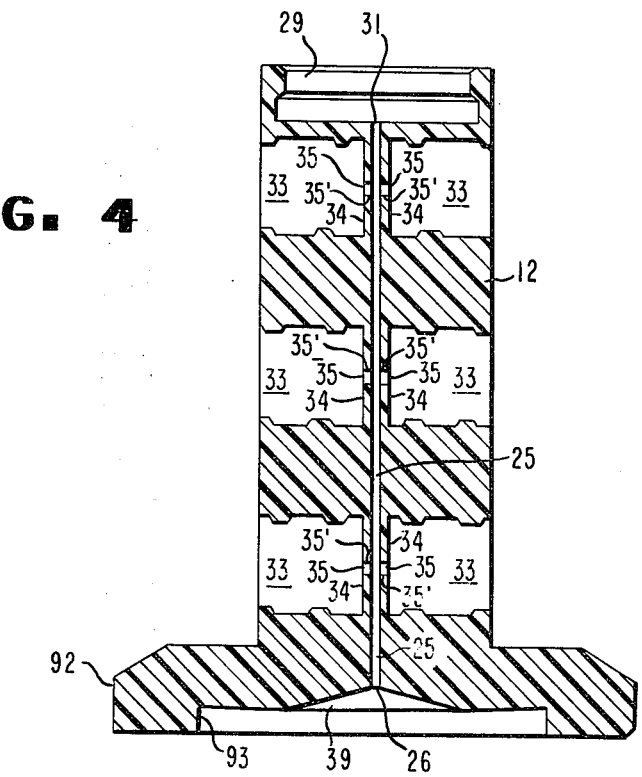
FIG. 4 is a cross-sectional front view of the housing used in the multi-valve assembly shown in FIGS. 1, 2 and 3.

Housing 12 is shown in cross-sectional view in FIGS. 3 and 4. This housing can be made from any suitable material such as stainless steel or aluminum. It may, however, be made from a plastic, such as an acrylic plastic, which decreases its costs. It contains a primary channel 25, a first end of which terminates at a pump orifice 26; and an output channel 27, a first end of which terminates at an intake/output orifice 28. Both orifices are located on the surface of the housing. Also located in the housing is a first blind recess 29, the bottom of which comprises a first valve seat 30 containing first and second orifices, 31 and 32, which are spaced in close proximity to one another. Orifice 31 is connected to the second end of the primary channel 25, and orifice 32 is connected to the second end of output channel 27.

Also included in the housing are a plurality of secondary blind recesses 33, each of which terminates in a secondary valve seat 34. Each secondary valve seat contains two orifices, 35 and 36, spaced in close proximity to one another. Secondary channels 35' are provided in opposing pairs to connect each one of orifice 35 to the primary channel 25. Also provided are a plurality of input channels 37, one ends of each of which are connected to orifices 36 and the other ends of each of which are connected to input orifices 38 located on the surface of the housing. Finally, the housing contains an additional blind recess 39, which in this embodiment, is a conical recess. Pump orifice 26 is located at the bottom of this additional blind recess 39.

Figure 5:
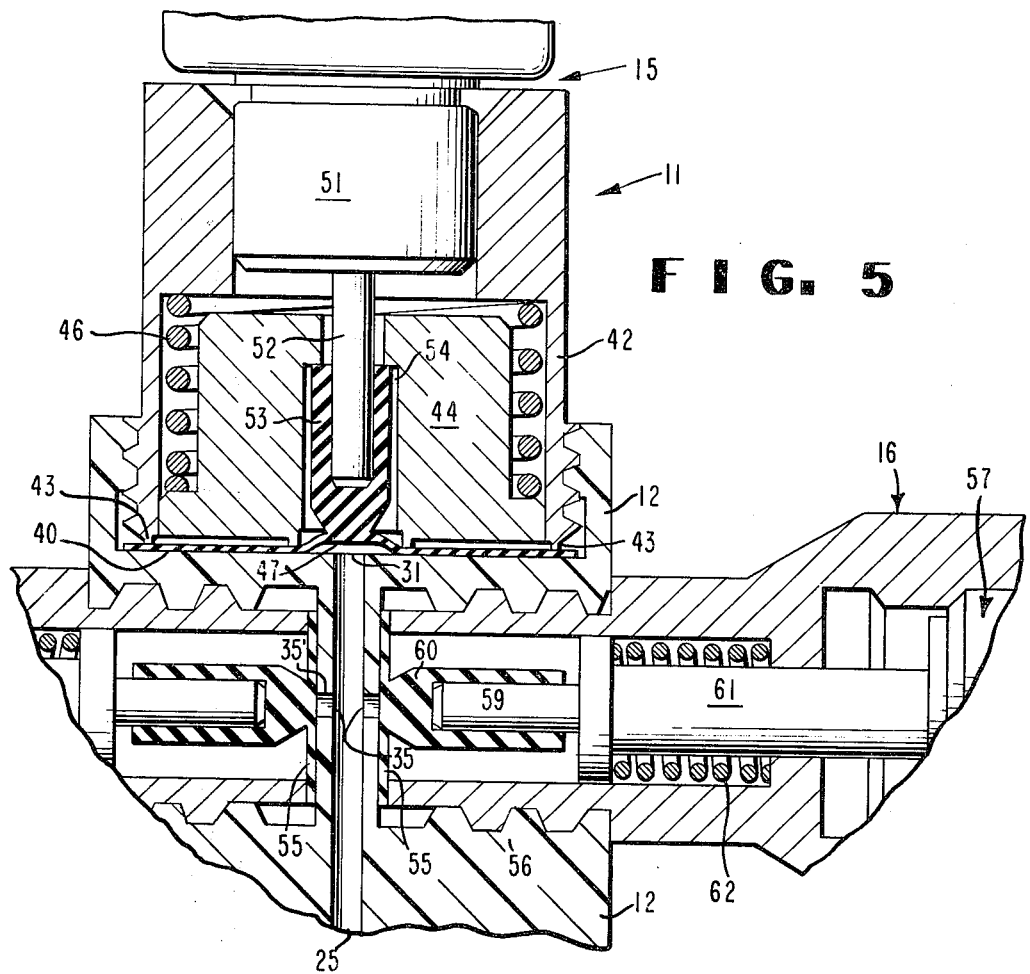
FIG. 5 is an expanded cross-sectional view of the housing and associated valve structure used in the multi-valve assembly shown in the preceding figures.

The internal structure of the valve is shown in FIG. 5. Connected to the top of housing 12 are the remaining portions of the first valve seat 30. This includes a first chamber forming means, which in the embodiment shown, comprises a flexible first diaphragm 40 held into contact with the first valve seat, at its periphery, by collar 42. In the embodiment shown, recess 29 is a threaded recess and collar 42 is a threaded collar which screws into the blind recess and compresses diaphragm 40 into contact with the valve seat by means of annular ridge 43. Located within collar 42 is a delimiting means which comprises a plug 44 with an annular ridge 45 and a recess 54. Annular ridge 45 is concentric with and inside annular ridge 43. It is compressed against diaphragm 40 by spring 46. Annular ridge 45 has a diameter such that the first and second orifices (orifice 31 and 32) of the first valve seat are located within it.

First flexible diaphragm 40 coacts with first valve seat 30 to form a leak-tight first chamber 47 connecting the first and second orifices (31 and 32) of the first valve seat. The delimiting means limits the extent of this chamber so that, in its normal condition, it only connects the first and second orifices together and provides no connection between the first and second orifices and the third orifice 48 of the first valve seat. Also included in the housing 12 is a relief channel 49, one end of which is connected to the third orifice 48 in the first valve seat, and the other end of which is connected to a drain orifice 50 in the surface of the housing.

Spring 46 coacts with plug 44 and collar 42 to force annular ridge 45 into contact with flexible diaphragm 40. However, if the pressure in the first chamber exceeds a certain value, plug 44 will retract, compressing spring 46, so that the first chamber 47 expands to include not only first and second orifices 31 and 32, but also third orifice 48 of the first valve seat. This mechanism provides a pressure relief system. If sufficient fluid pressure builds up in the system, rather than rupture diaphragm 40, delimiting means will be forced to retract and the fluid pressure will be relieved by the passage of fluid through relief channel 49 into a drain (not shown).

The first valve structure also comprises a first means 51 to move diaphragm 40 to close off the connection between the first and second orifices 31 and 32 of the first valve seat by collapsing the chamber connecting them. In the embodiment shown, this first means to move comprises a solenoid with a movable rod 52 connected to the first diaphragm 40 by a connecting stub 53 on the diaphragm. In the embodiment shown, the solenoid is positioned so that in its deactivated state, diaphragm 40 is pulled away from recesses 31 and 32 to form a distinct chamber 47 connecting the two orifices. The extent of this chamber is limited by the diameter of flange 45 and the extent to which the base of recess 54 allows the end of stub 53 to be retracted by rod 52.

The secondary valve structure consists of a flexible secondary diaphragm 55 connected at its periphery to the secondary valve seat by means of an annular flange 56 which compresses the diaphragm against the valve seat. Diaphragms 55 as well as diaphragm 40 can be made from any suitably flexible, inert material such as neoprene. The flexible diaphragm coacts with the secondary valve seat to form a leak-tight secondary chamber connecting the first and second orifices 35 and 36 of the secondary valve seat together. Flange 56 is connected to solenoid 57 which forms the secondary means to move the secondary diaphragm. The secondary means to move the secondary diaphragm also consists of a plug 58 with a rod 59 coacting with a stub 60 which is part of the flexible diaphragm. Plug 58 coacts with the plunger 61 of solenoid 57 and is spring loaded by spring 62. In its normal deactivated position, the solenoid is positioned so that the flexible diaphragm is pressed against the secondary valve seat. Normally, then, the chamber connecting orifices 35 and 36 is closed. However, solenoid 57 can be activated to retract the central portion of the diaphragm and form a chamber connecting the orifices 35 and 36 so that secondary fluid can be drawn from its source 19 through intake lines 37 and into the primary channel 25 through secondary channel 35'.

One embodiment of the entire liquid sampling assembly is shown in FIG. 1. The multi-valve assembly of FIGS. 2, 3 and 5 is shown attached to the pump assembly 24. The pump, which is shown in cross-section, includes a support 90 which supports both the pump and the drive for the pump. The pump itself comprises a cylinder 91 which is externally threaded at its upper end. The base 92 of multi-valve assembly 11 consists of an internally threaded recess 93 which engages the pump. This recess is relieved (about 2°) as shown in FIG. 3 so that a seal is made between the pump cylinder and the edge of the conical recess 39. Alternatively, an externally threaded base coupled to the pump cylinder by an internally threaded rotating collar can be used. Located at the bottom of cylinder 91 is a cap 64 which is connected to the cylinder by screws 65. Running through the cylinder 91 is a piston rod 68, one end of which is movably mounted in support 90 by bearing 69. Piston 68 is movably mounted within cylinder 91, and held in leak-tight association with the cylinder by O-rings 66 and 73 and spacer 67. At the other end of piston rod 68 is located a cap assembly 70 which terminates in a conical cap 71. The conical surface of cap 71 is designed to mate with the concave recess 39 in the base of multi-wave housing 12. O-rings 72 and 73 are provided so that piston rod 68 is mounted in movable yet leak-tight association with cylinder 91. Hence, by withdrawing piston rod 68, fluid can be pulled in through probe 17, or from the source of secondary liquid 20, depending upon which valve in the multi-valve assembly is open.

Any suitable mechanism can be used to remove the piston rod in cylinder 91. As shown in this embodiment, however, rod 74 is mounted in the hollow of support 90 by means of ball bearing 75 and 75' and lock washers 76 and 76'. Ball bearing 75' is supported in bearing housing 94 which is connected to support 90. Rod 74 can be rotated by a belt 77 which operates on a pulley 78 attached to one end of the rod. The mechanism for moving the belt, generally a motor, is not shown. Rod 74 is a threaded rod which is designed to engage a threaded yoke 79. The details of yoke 79 will not be described in detail because they do not form part of the present invention. Generally, however, the yoke consists of a threaded bearing attached to the yoke and threadedly engages rod 74. The purpose of yoke 79 is to move piston rod 68. This is done by providing an arm 80 which is attached to yoke 79. Arm 80 is in turn attached to piston rod 68 and carries with it a micrometer 81. The face of micrometer 81 is designed to mate with a microswitch 82, which is used to electrically deactivate the motor which drives belt 77 when the piston rod reaches the desired position. By changing the setting of micrometer 81, the position of the piston rod when the motor is disengaged can be altered at will. Piston rod 68 fits through a hole in arm 80 or yoke 79 and is clamped into position by split collars 83, a fluid jacket 84 and spring clip 83'. As collars 83 are brought into contact with one another, spring clip 83' forces fluid jacket 84 into contact with arm 80. The O-rings are provided in fluid jacket 84. This forms a leak-tight chamber around opening 86 in piston rod 68. This opening 86 in cooperation with uppermost opening 86' in the piston provides a backwash system as described in U.S. Pat. No. 3,612,360. Finally, screw rod 74 is spring loaded by means of fitting 96 and resilient bearing 97 so that if the piston rod is driven too far, the advance system will give rather than than cause damage to the remaining structure.

In a preferred embodiment, secondary channels 35' which connect the secondary valves to primary channel 25 are provided in opposing pairs. One of the most persistent problems in high precision sampling is "carryover" of a previous sample, or diluent, to a subsequent test. For this reason, various flushing or purging steps are used in almost all high precision work. However, because of the convoluted nature of the channels used in such sampling systems, complete purging of the connecting lines is difficult. It has been found that if the secondary channels 35' are provided in opposing pairs, turbulence which occurs at the connection of these channels to the primary channel 25 aids in cleansing these channels. As far as the purging liquid is concerned, these channels are blind channels. Each alone is difficult to flush. But in opposing pairs, normal flushing procedures are effective to flush secondary channels as well as the primary channel.

The operation of the present fluid handling system is similar to that described with regard to the system disclosed in U.S. Pat. No. 3,612,360 which issued on Aug. 16, 1968; the relative portions of which are hereby incorporated by reference in the present application. In the present system, however, the secondary valves are not non-pumping valves. The need for this is avoided by having the first valve closed during the interval when the secondary valves are moving.

The above description is intended to exemplify only one embodiment of the present invention. A number of modifications apparent to one skilled in the art can be made to the present invention. For example, rather than use a flexible diaphragm to form the leak-tight chamber which connects the orifices in the first and secondary valves, any kind of chamber-forming means which will coact with the valve seat to form the leak-tight chamber, and any type of closure means which is movably mounted in the chamber and has a resilient surface to mate with the valve seat can be used. Furthermore, in place of the solenoids, any means to move the resilient surface of the closure means into contact with the valve seat to close off the connection between the orifices in that valve seat can be used. Furthermore, although the present invention is described with regard to a piston pump, any type of pump suitable for the purpose to which the fluid sampling assembly is directed can be used.

What is claimed is:

1. A fluid handling assembly comprising:
   a. a housing;
   b. a primary channel in said housing, a first end of which terminates at a pump orifice on the surface of said housing;
   c. an output channel in said housing, a first end of which terminates at an intake/output orifice on the surface of said housing;
   d. a first valve structure comprising
      i. a first valve seat disposed in said housing and containing first and second closely spaced orifices, one orifice being connected to the second end of said primary channel and the other orifice being connected to the second end of said output channel;
      ii. a flexible first diaphragm connected at its periphery to said housing and coacting with said first valve seat to form a leak-tight first chamber connecting the first and second orifices of said first valve seat; and iii. first means to move said first diaphragm to close off the connection between the first and second orifices of said first valve seat;

e. at least one secondary valve structure comprising i. a secondary valve seat located on the surface of said housing and containing two closely spaced orifices;

ii. a secondary channel, connecting one orifice of said secondary valve seat to said primary channel;

iii. an input channel, connecting the other orifice of said secondary valve seat to an input orifice located on the surface of said housing;

iv. a flexible secondary diaphragm connected at its periphery of said secondary valve seat to form a leak-tight secondary chamber connecting the orifices of said secondary valve seat;

v. secondary means to move said secondary diaphragm to close off the connection between the orifices of said secondary valve seat;

f. a relief channel having one end terminating in a drain orifice on the surface of said housing and the other end terminating in a third orifice in said first valve seat, said third orifice being within the periphery of said first diaphragm but spaced relatively distant from the first and second orifices of said first valve seat; and g. delimiting means coacting with said first diaphragm to press the perpiheral portions of said first diaphragm into contact with said valve seat and limit the extent of said first chamber so that it connects only the first and second orifices of said first valve seat, said delimiting means being resiliently mounted to retract under sufficient pressure and expand said first chamber to include the third orifices of said first valve seat.

2. The multi-valve assembly of claim 1 comprising a plurality of secondary valve structures.

3. The multi-valve assembly of claim 1 wherein:

a. said first means to move is normally positioned so that said first valve structure is in a normally open mode; and b. said secondary means to move is normally positioned so that said secondary valve structure is in a normally closed mode.

4. The multi-valve assembly of claim 1 wherein said secondary channels are provided in opposing pairs.

5. The multi-valve assembly of claim 1 wherein said housing comprises:

a. a first blind recess, said first valve seat being located on the bottom surface of said first blind recess; and b. a plurality of secondary blind recesses, said secondary valve seats being located on the bottom surfaces of said secondary blind recesses.

6. The multi-valve assembly of claim 5 wherein said first means to move and said secondary means to move are solenoids.

7. The multi-valve assembly of claim 5 wherein said first blind recess and said secondary blind recesses are threaded recesses and wherein said first means to move and said secondary means to move threadedly engage said first and secondary blind recesses, respectively.

8. The multi-valve assembly of claim 2 further comprising a probe and a tube connecting said probe to said intake/output orifice.

9. The multi-valve assembly of claim 8 further comprising at least one source of secondary fluid and a tube connecting said source to said input orifice.

10. The multi-valve assembly of claim 9 further comprising a pump disposed adjacent and connected to said pump orifice.

11. The multi-valve assembly of claim 10 wherein said housing comprises an additional blind recess, said pump orifice being located in the bottom surface of said additional blind recess and said pump being located in said additional blind recess.

* * * * *